United States Patent [19]
Sugiyama et al.

[11] Patent Number: 6,156,176
[45] Date of Patent: Dec. 5, 2000

[54] AIR FUEL RATIO SENSOR WITH OXYGEN PUMP CELL

[75] Inventors: Tomio Sugiyama, Nagoya; Masahiro Sibata, deceased, late of Nagoya, by Midori Sibata, legal representative; Makoto Nakae, Toyoake, all of Japan

[73] Assignee: Denso Corporation, Japan

[21] Appl. No.: 09/201,104

[22] Filed: Nov. 30, 1998

[30] Foreign Application Priority Data

Dec. 4, 1997 [JP] Japan .................................. 9-352312

[51] Int. Cl.⁷ .................................................. G01N 27/407
[52] U.S. Cl. ........................ 204/425; 204/426; 204/427; 204/429
[58] Field of Search ...................... 204/421–429

[56] References Cited

U.S. PATENT DOCUMENTS

| | | | |
|---|---|---|---|
| 4,839,019 | 6/1989 | Takahama et al. | 204/425 |
| 4,861,456 | 8/1989 | Mase et al. | 204/429 |
| 4,882,033 | 11/1989 | Shibata et al. | |
| 5,174,885 | 12/1992 | Hayakawa et al. | 204/429 |
| 5,290,421 | 3/1994 | Reynolds et al. | 204/424 |
| 5,472,591 | 12/1995 | Saito et al. | 204/429 |
| 5,763,763 | 6/1998 | Kato et al. | 204/429 |
| 5,766,434 | 6/1998 | Fujii et al. | 204/429 |

FOREIGN PATENT DOCUMENTS 60-78340  5/1985  Japan .

*Primary Examiner*—T. Tung
*Attorney, Agent, or Firm*—Nixon & Vanderhye PC

[57] ABSTRACT

First and second solid electrolyte bodies are opposed to one another to form a reference gas chamber therebetween. A measurement cell for detecting an air fuel ratio in measurement gas is provided on the first solid electrolyte body with a measurement electrode exposed to the measurement gas and a reference electrode exposed to the reference gas chamber. An oxygen pump cell is provided on the second solid electrolyte body with a first pump electrode exposed to the measurement gas and a second pump electrode exposed to the reference gas chamber. When a voltage is applied to the first and second oxygen pump cell, the oxygen gas is introduced from the measurement gas into the reference gas chamber.

20 Claims, 3 Drawing Sheets

AIR FUEL RATIO SENSOR WITH OXYGEN PUMP CELL

CROSS REFERENCE TO RELATED APPLICATION

This application is based upon and claims the benefit of priority of the prior Japanese Patent Application No. 9-352312, filed on Dec. 4, 1997, the contents of which are incorporated herein by reference.

BACKGROUND OF THE INVENTION

1. Field of the Invention

This invention relates to an air fuel ratio sensor which is installed in an exhaust system of an automotive internal combustion engine for controlling an air fuel ratio of the internal combustion engine.

2. Description of the Related Art

Conventionally, an air fuel ratio sensor is installed in an exhaust system of an automotive internal combustion engine to control an air fuel ratio. As shown in FIG. 1, the air fuel ratio sensor 9 is typically composed of a solid electrolyte body 131 having oxygen ion conductivity, a measurement electrode 111 disposed on the front surface of the electrolyte body 131, a reference electrode 112 disposed on the back surface of the electrolyte body 131, and a reference gas chamber 10 in which the reference electrode 112 is disposed. The air fuel ratio sensor 9 further has a heater 15 including a heating resistor 150.

The air fuel ratio sensor 9 is the so-called limiting current type oxygen sensor. That is, when a voltage is applied across the measurement electrode 111 and the reference electrode 112, this type of the air fuel ratio sensor provides output current characteristics with a flat portion with respect to the voltage. The flat portion represents a limiting current value corresponding to an oxygen gas concentration contained in measurement gas. Then, the air fuel ratio is detected based on the oxygen gas concentration. Therefore, it is desired for the air fuel ratio sensor that the output current characteristics clearly have the flat portion with respect to the voltage in a wide range to precisely detect the limiting current value.

In the conventional structure of the air fuel ratio sensor, however, when the air fuel ratio is shifted to a rich side so that the oxygen gas concentration in exhaust gas (measurement gas) decreases, the output current of the air fuel ratio sensor readily changes in response to the change in voltage not to have the flat portion corresponding to the limiting current value. As a result, the oxygen gas concentration and the air fuel ratio may not be precisely detected.

In more detail, when the oxygen gas concentration in the measurement gas is decreased to some extent, the output current flowing between the measurement electrode and the reference electrode is increased so largely that the oxygen gas introduced into the reference gas chamber becomes short. At that time, the output current cannot clearly have the flat portion with respect to the voltage.

SUMMARY OF THE INVENTION

The present invention has been made based on the above problem. An object of the present invention is to provide an air fuel ratio sensor capable of precisely detecting an air fuel ratio even when an oxygen gas concentration in measurement gas is decreased.

According to the present invention, in an air fuel ratio sensor for detecting an air fuel ratio of measurement gas using reference gas introduced into a reference gas chamber formed therein, a measurement cell for detecting the air fuel ratio is provided on a solid electrolyte body having oxygen ion conductivity. Further, an oxygen pump cell is provided on the solid electrolyte body for introducing oxygen gas from the measurement gas into the reference gas chamber. The oxygen pump cell has a first pump electrode which is disposed on a first surface of the solid electrolyte body to be exposed to the measurement gas and a second pump electrode which is disposed on a second surface of the solid electrolyte body to be exposed to the reference gas chamber. The first pump electrode faces the second pump electrode with the solid electrolyte body interposed therebetween.

Accordingly, when a voltage is applied to the oxygen pump cell, the oxygen gas contacting the first pump electrode is decomposed to be oxygen ions, and the oxygen ions flows in the solid electrolyte body toward the second pump electrode and return to the oxygen gas on the second pump electrode. Thus, the oxygen gas is introduced into the reference gas chamber. Therefore, even when an oxygen gas concentration in the measurement gas is decreased so that a large amount of oxygen gas flows out from the reference gas chamber as an ion current, the oxygen gas is sufficiently supplied into the reference gas chamber by the oxygen pump cell. As a result, output current characteristics of the sensor can always have a flat portion corresponding to a limiting current value, so that the oxygen gas concentration can be precisely detected.

The voltage applied to the oxygen pump cell is preferably equal to or less than 1V. When the voltage exceeds 1 V, the solid electrolyte body may be damaged especially when it is made of zirconia. Preferably, the air fuel ratio sensor has a heating member electrically connected to the oxygen pump cell. Accordingly, the oxygen pump cell and the heating member can be simultaneously driven by an electric power using common lead portions, resulting in simple structure of the sensor.

BRIEF DESCRIPTION OF THE DRAWINGS

Other objects and features of the present invention will become more readily apparent from a better understanding of the preferred embodiments described below with reference to the following drawings.

DETAILED DESCRIPTION OF THE PREFERRED EMBODIMENTS (First Embodiment)

Figure 1:
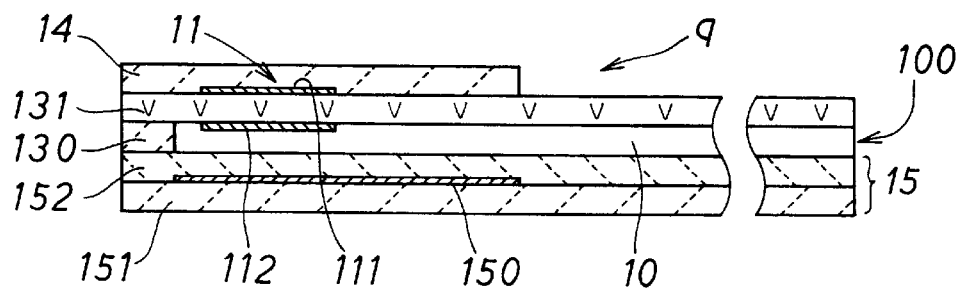
FIG. 1 is a cross-sectional view showing a prior art air fuel ratio sensor.

A first preferred embodiment of the present invention will be explained referring to FIGS. 2–5. Herebelow, the same parts as those of the air fuel ratio sensor 9 shown in FIG. 1 are indicated with the same reference numerals.

Figure 2:
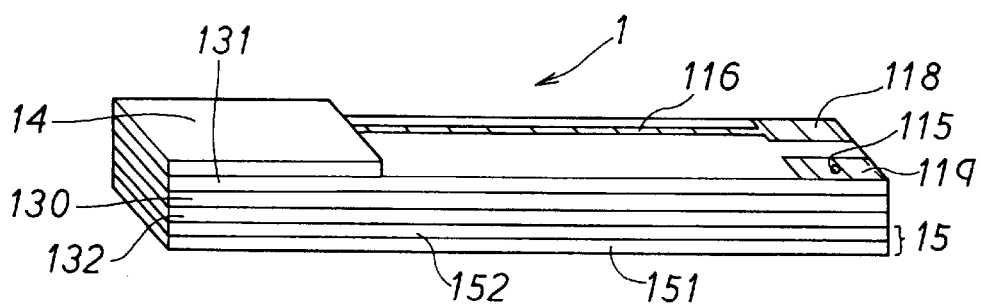
FIG. 2 is a perspective view showing an air fuel ratio sensor, according to a first preferred embodiment of the present invention.
Figure 3:
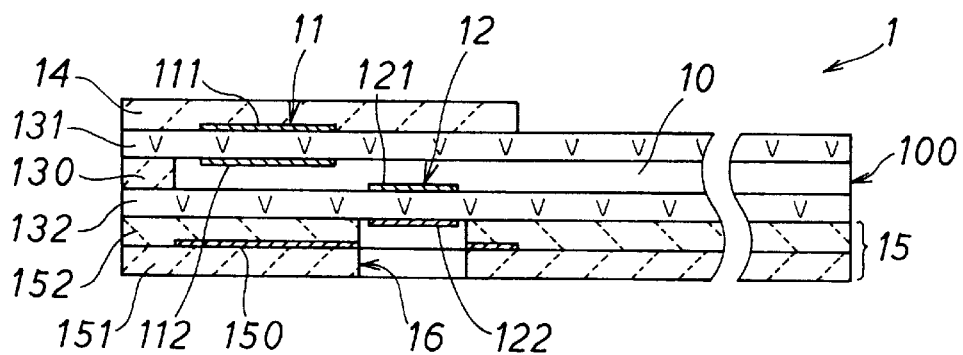
FIG. 3 is a cross-sectional view showing the air fuel ratio sensor of the first embodiment.
Figure 4:
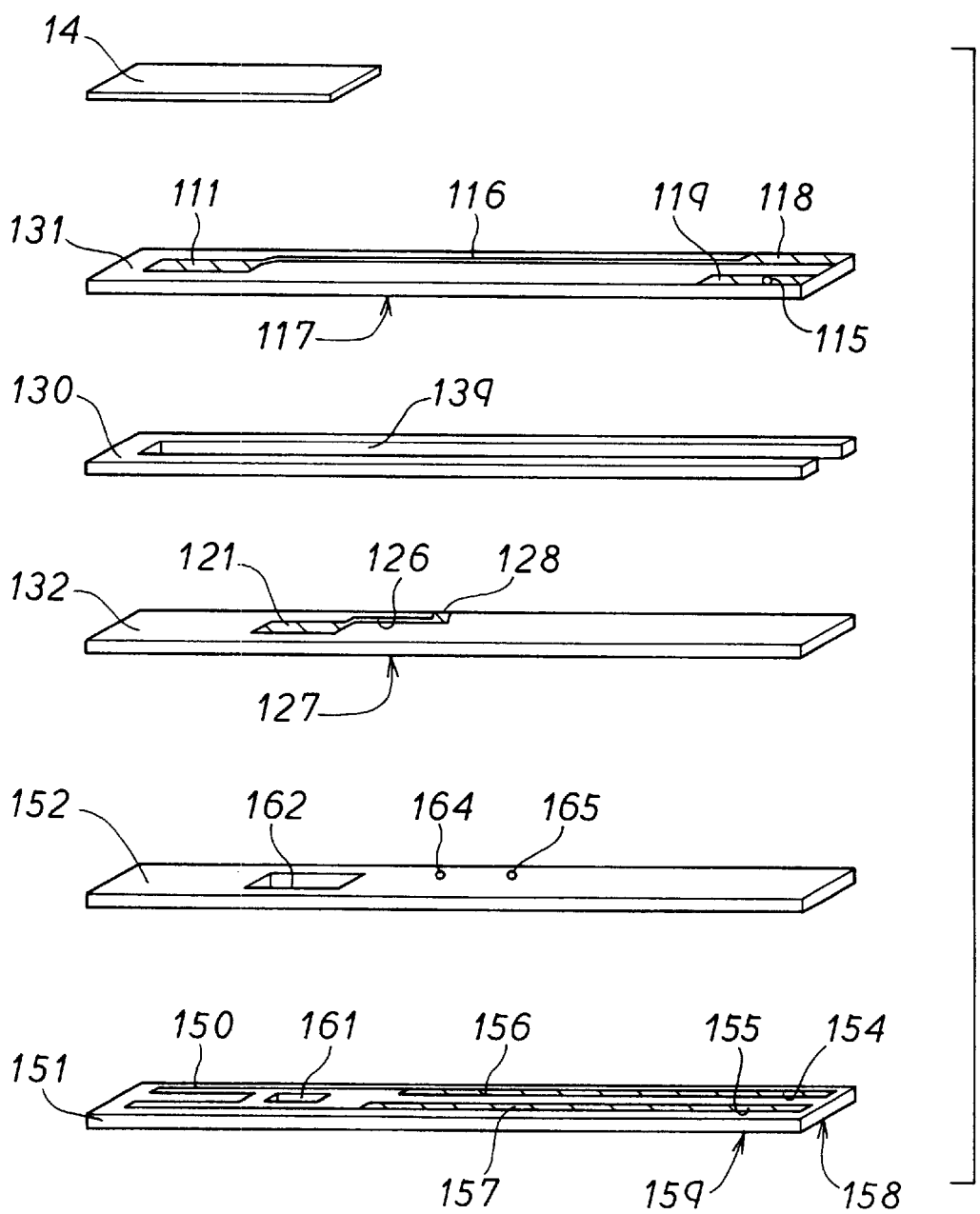
FIG. 4 is an exploded view showing the air fuel ratio sensor of the first embodiment.

As shown in FIGS. 2–4, an air fuel ratio sensor 1 in the first embodiment has a first solid electrolyte body 131, a chamber defining plate 130 for defining a reference gas chamber 10, a second solid electrolyte body 132, and a heater 15, which are integrally laminated with one another in this order. The first and second solid electrolyte bodies 131, 132 have oxygen ion conductivity.

The first solid electrolyte body 131 has a measurement cell 11, which is composed of a measurement electrode 111 disposed on a main surface of the electrolyte body 131 to be exposed to measurement gas and a reference electrode 112 provided on a back surface of the electrolyte body 131 to be exposed to the reference gas chamber 10. The measurement electrode 111 and the reference electrode 112 are opposed to one another with the electrolyte body 131 interposed therebetween. The surface of the measurement electrode 111 is covered with a gas diffusion resistive layer 14 for restricting the measurement gas from being introduced onto the measurement electrode 111. As shown in FIG. 4, the measurement electrode 111 is electrically connected to a terminal 118 through a lead portion 116. The reference electrode 112 is electrically connected to a terminal 119 provided on the main surface of the electrolyte body 131 through a lead portion 117 provided on the back surface of the electrolyte body 131 and a through hole 115. The terminals 118, 119 are connected to lead wires and the like (not shown) so that an output signal of the measurement cell 11 can be taken out. The output signal of the measurement cell 11 corresponds to the output signal of the air fuel ratio sensor 1.

The reference gas chamber 10 is defined by the first and second solid electrolyte bodies 131, 132 opposite to one another and the chamber defining plate 130 intervening between the electrolyte bodies 131, 132. As shown in FIG. 4, the chamber defining plate 130 has a groove portion 139 for defining the reference gas chamber 10. An opening end of the reference gas chamber 10 serves as an air introduction port 100 for introducing atmospheric air as reference gas into the chamber 10 utilizing natural convection.

The second solid electrolyte body 132 has an oxygen pump cell 12 for pumping oxygen gas from the measurement gas (exhaust gas) into the reference gas chamber 10. The oxygen pump cell 12 is composed of a pair of pump electrodes 121, 122. The pump electrode 121 is exposed to the reference gas chamber 10, while the pump electrode 122 is exposed to an exhaust gas introduction groove 16. Referring again to FIG. 4, the pump electrode 121 is electrically connected to a lead portion 156 of the heater 15 described below, through a lead portion 126 and a through hole 128 of the second solid electrolyte body 132, and a through hole 164 of a cover plate 152 of the heater 15. The pump electrode 122 is electrically connected to a lead portion 157, which is also provided on the heater 15, through a lead portion 127 of the electrolyte body 132 and a through hole 165 of the cover plate 152.

The heater 15 is composed of a heater substrate 151, a heating resistor (heating member) 150 disposed on the heater substrate 151, and the cover plate 152 laminated with the heater substrate 151 to cover the heater substrate 151 and the heating resistor 150. When the air fuel ratio sensor 1 is projectively observed, the heating resistor 150 is provided at a position covering the measurement electrode 111, the reference electrode 112, and the pump electrodes 121, 122. Further, the heater 15 has the exhaust gas introduction groove 16 facing the pump electrode 122 as described above. The exhaust gas introduction groove 16 is composed of window portions 161, 162 respectively provided in the heater substrate 151 and the cover plate 152.

The heating resistor 150 is electrically connected to terminals 158, 159 through the lead portions 156, 157 and through holes 154, 155 of the heater substrate 151. The terminals 158, 159 are connected to an external power supply through lead wires and the like (not shown). Incidentally, the pump electrode 122 exposed to the exhaust gas introduction groove 16 electrically communicates with the terminal 159 on a high voltage side through the lead portion 127, and the external power supply is controlled so that a potential difference between the lead portions 126 and 127, i.e., between the pump electrodes 121 and 122 is less than 1V.

Next, a measurement method of the air fuel ratio sensor 1 in the present embodiment will be explained. First, a process for forming zirconia sheets for the first and second solid electrolyte bodies 131, 132 will be explained. Specifically, ceramic mixture composed of partially stabilized yttria-zirconia which includes 6 mol % yttria and 94 mol % zirconia, α-alumina, poly vinyl butyral (PVB), dibutyl phthalate (DBP), ethanol, and toluene is prepared. The mixing ratios by weight are as follows. That is, when the partially stabilized yttria-zirconia is 100 by weight, α-alumina is 1, PVB is 5, DBP is 10, ethanol is 10, and toluene is 10, respectively. An average particle diameter of the partially stabilized yttria-zirconia is 0.5 μm.

Next, the ceramic mixture is mixed by a ball mill to be slurry. The thus obtained slurry is formed into a sheet member by a doctor blade method so that the sheet member can have a thickness of approximately 0.3 mm after dried. The sheet member is cut into rectangular sheets respectively having a size of 5 mm×70 mm. The through hole 115 is formed in one of the rectangular sheets, and Pt paste including zirconia is applied to the sheet by a screen printing method for the measurement electrode 111, the reference electrode 112, the lead portions 116, 117 and the terminals 118, 119. In this way, the sheet for the first solid electrolyte body 131 is formed. Likewise, the through hole 128 is formed in another one of the rectangular sheets, and the Pt paste including zirconia is applied to the sheet by the screen printing method for the pump electrodes 121, 122, and the lead portions 126, 127. In this way, the sheet for the second solid electrolyte body 132 is formed.

Successively, a process for forming alumina sheets for the chamber defining plate 130, the cover plate 152, and the heater substrate 151 will be explained. Specifically, ceramic mixture composed of α-alumina having an average particle diameter of 0.2 μm, partially stabilized yttria-zirconia which includes 6 mol % yttria and 94 mol % zirconia, PVB, DBP, ethanol, and toluene are prepared. The mixing ratios by weight are as follows. That is, when the α-alumina is 98 by weight, the partially stabilized yttria-zirconia is 3, PVB is 10, DBP is 10, ethanol is 30, and toluene is 30, respectively.

Next, the ceramic mixture is mixed by the ball mill to be slurry, and the slurry is formed into a sheet member having a thickness of 0.3 mm after dried. The sheet member is cut into rectangular sheets respectively having a size of 5 mm×70 mm. The through holes 154, 155 and the window portion 161 with a size of 2 mm×8 mm are formed in one of the sheets. Further, Pt paste including alumina is applied to the sheet by the screen printing method for forming the heating resistor 150, the lead portions 156, 157, and the terminals 158, 159. Accordingly, the sheet for the heater substrate 151 is formed.

The sheet for the cover plate 152 is formed from another one of the rectangular sheets by forming the through holes 164, 165 and the window portion 162 with a size of 2 mm×8 mm in the sheet and by filing the through holes 164, 165 with the Pt paste including zirconia. The sheet for the chamber defining plate 130 is further formed from another one of the rectangular sheets by forming the groove portion 139 having a size of 2 mm×65 mm therein so that the remaining sheet has a U shape as shown in FIG. 4.

Next, a process for forming an alumina sheet for the gas diffusion resistive layer 14 will be explained. First, ceramic mixture composed of α-alumina having an average particle diameter of 0.3 μm, PVB, DBP, ethanol, and toluene is prepared. Concerning the mixing ratios by weight, when α-alumina is 100 by weight, PVB is 10, DBP is 10, ethanol is 30, and toluene is 30, respectively. Then, the ceramic mixture is mixed by the ball mill to be slurry, and the slurry is formed by the doctor blade method into a sheet member which can have a thickness of 0.2 mm after dried. The alumina sheet for the gas diffusion resistive layer 14 is formed by cutting the alumina sheet member to have a size of 5 mm×25 mm.

The sheets for the gas diffusion resistive layer 141, the first solid electrolyte body 131, the chamber defining plate 130, the second solid electrolyte body 132, the cover plate 152, and the heater substrate 151 are laminated with one another in this order as shown in FIG. 4, and are joined together by pressure using paste, which has pressure sensitive adhesive property at a room temperature, thereby forming a lamination body. The lamination body is sintered in atmosphere for one hour at approximately 1500° C. As a result, the air fuel ratio sensor 1 is completed.

Next, characteristics of the air fuel ratio sensor 1 in the present embodiment were examined as compared with the air fuel ratio sensor 9 shown in FIG. 1 as a comparative sample. The air fuel ratio sensor 9 used as the comparative example has generally the same structure as that of the air fuel ratio sensor 1 in the present embodiment, except that the air fuel ratio sensor 9 does not have the oxygen pump cell 12 and the second solid electrolyte body 132. In the air fuel ratio sensor 9, the reference gas chamber 10 is defined by the heater 15 and the solid electrolyte body 131 facing one another and the chamber defining plate 130.

Then, V-I characteristics of the air fuel ratio sensors 1, 9 described above were measured under conditions where the air fuel ratio was in a range of 9–18, and accordingly limiting current characteristics were evaluated. A volume of a combustion chamber of an engine used in this evaluation test was 2 lit. Combustion conditions of the engine were appropriately controlled during the evaluation test so that the temperature of the exhaust gas was kept at 400° C. and the temperature of the air fuel ratio sensor was kept at 750° C. The air fuel ratio of the exhaust gas was controlled to be in a range of 9–18.

Figure 5:
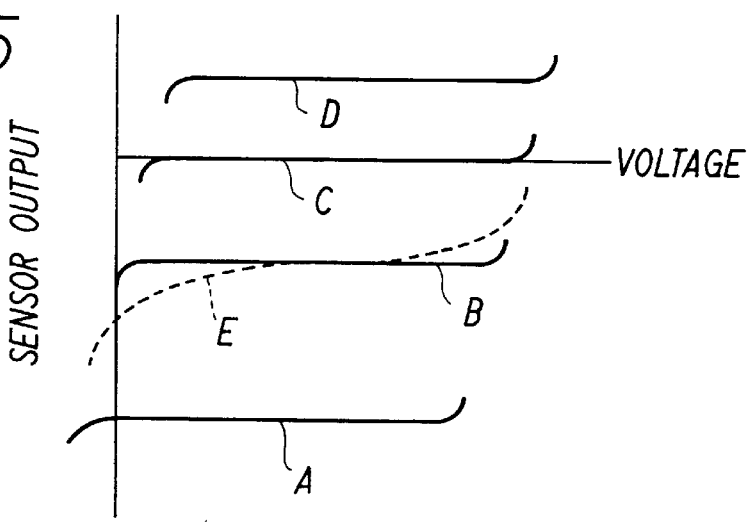
FIG. 5 is a graph showing limiting current characteristics of the air fuel ratio sensor of the first embodiment and the air fuel ratio sensor shown in FIG. 1.

The results of the evaluation test are shown in. FIG. 5. In the figure, a vertical axis indicates output current of the sensor, and a horizontal axis indicates the voltage applied between the measurement electrode and the reference electrode. Curves A–D were obtained from the air fuel ratio sensor 1 in the present embodiment, while curve E was obtained from the air fuel ratio sensor 9 as the comparative example. More specifically, the curve A was obtained when the air fuel ratio was 9, the curves B, E were obtained when the air fuel ratio was 12, the curve C was obtained when the air fuel ratio was 14.5, and the curve D was obtained when the air fuel ratio was 18. Incidentally, the boundary value of the air fuel ratio between a rich side and a lean side is generally 14.5.

As understood from FIG. 5, the output current curves (A–D) of the air fuel ratio sensor 1 in the present embodiment always had flat portions corresponding to limiting current values when the air fuel ratio was in the range of 9–18. As opposed to this, when the air fuel ratio was 12, the output current curve (E) of the air fuel ratio sensor 9 hardly had a flat portion corresponding to the limiting current value. Accordingly, it is confirmed that the air fuel ratio sensor 1 having the oxygen pump cell 12 can precisely detect the air fuel ratio even when the oxygen gas concentration in the measurement gas is low. It is further confirmed that the air fuel ratio sensor 9 cannot precisely detect the air fuel ratio when the air fuel ratio is 12 or more.

Next, the effects of the air fuel ratio sensor 1 in the present embodiment will be explained in more detail. As described above, the air fuel ratio sensor 1 has the oxygen pump cell 12 for introducing the oxygen gas from the measurement gas into the reference gas chamber 10. The pump electrodes 121, 122 of the oxygen pump cell 12 are disposed to contact the reference gas chamber 10 and the measurement gas, respectively. Further, the pump electrodes 121, 122 are respectively connected to the lead portions 156, 157 of the heating resistor 150, and a voltage is applied between the pump electrodes 121, 122 through the lead portions 156, 157.

When the voltage is applied between the pump electrodes 121, 122, the oxygen gas is decomposed (ionized) to produce oxygen ions on the surface of the pump electrode 122 contacting the measurement gas, and the oxygen ions moves toward the pump electrode 121 in the reference gas chamber 10 through the second solid electrolyte body 132. Then, the oxygen ions are oxidized to return to the oxygen gas on the pump electrode 121. In this way, the oxygen gas is introduced from the measurement gas into the reference gas chamber 10 by the oxygen pump cell 12 so that a sufficient amount of the oxygen gas is always held in the reference gas chamber 113.

Therefore, in the air fuel ratio sensor 1, even when the oxygen gas concentration of the measurement gas is decreased, the oxygen ion current from the reference gas chamber 10 is prevented from being stopped or decreased. As a result, the output current characteristics have the flat portion with respect to the voltage, whereby the oxygen gas concentration and the air fuel ratio can be precisely detected. Here, it should be noted that the pump electrodes of the oxygen pump cell have acitivity capable of ionizing the oxygen gas, and include for example Pt, Pt/Rh, Pt/Pd or the like.

Also, in the air fuel ratio sensor 1 of the present embodiment, the measurement cell 11 and the oxygen pump cell 12 are disposed on the respective solid electrolyte bodies 131, 132. Because of this, the oxygen ion current flowing in the measurement cell 11 and the oxygen ion current flowing in the oxygen pump cell 12 do not interfere with one another. In addition, because the oxygen pump cell 12 is provided on the side of the heater 15, the activation of the oxygen pump cell 12 can be enhanced so that the oxygen pump cell 12 works with high efficiency.

The oxygen pump cell 12 electrically communicates with the lead portions 156, 157 so that it electrically communicates with the external power supply or the like. Accordingly, it is not necessary to form extra lead portions for the oxygen pump cell 12, resulting in size reduction of the air fuel ratio sensor 1. Further, the structure is simplified so that the manufacturing process becomes easy and the manufacturing cost is reduced.

Incidentally, it is sufficient for the oxygen pump cell 12 to have the pump electrodes which are exposed to the reference gas chamber 10 and the measurement gas, respectively, in order to introduce the oxygen gas from the measurement gas into the reference gas chamber 10. That is, the oxygen pump cell 12 can be provided on the first solid electrolyte body 131 together with the measurement cell 11. Further, it is not always necessary that the oxygen pump cell 12 introduce the oxygen gas from the measurement gas into the gas reference chamber 10. The oxygen pump cell 12 can introduce the oxygen gas from outside fluid flowing outside of the gas reference chamber 10 other than the measurement gas. At that time, the pump electrode 122 is exposed not to the measurement gas but to the outside fluid.

Figure 6:
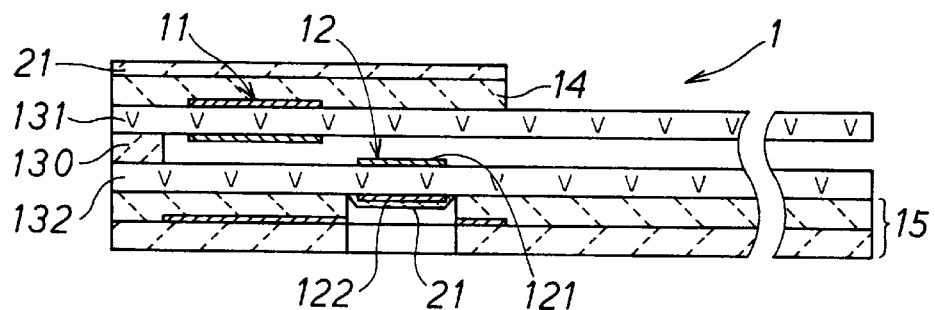
FIG. 6 is a cross-sectional view showing a modified example of the air fuel ratio sensor of the first embodiment.

As shown in FIG. 6, the surfaces of the gas diffusion resistive layer 14 and the pump electrode 122, both of which are exposed to the measurement gas, may be covered with a trap layer 21. The trap layer 21 is preferably made of ceramic material. Accordingly, the measurement electrode 111 and the pump electrode 122 can be prevented from being deteriorated by contaminations in the measurement gas.

(Second Embodiment)

Figure 7:
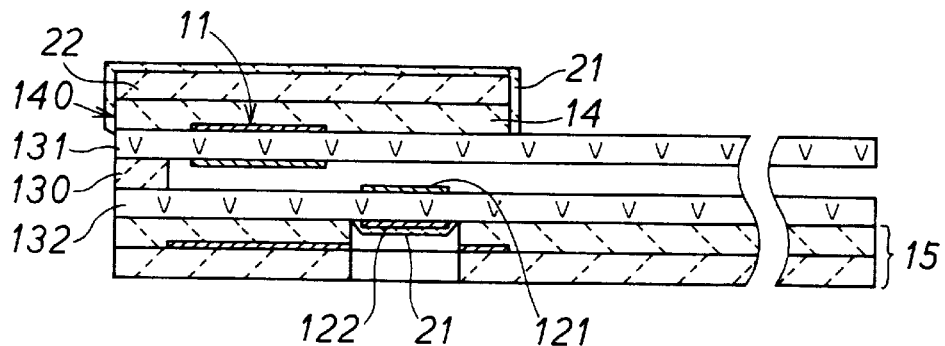
FIG. 7 is a cross-sectional view showing an air fuel ratio sensor according to a second preferred embodiment.

In a second preferred embodiment, as shown in FIG. 7, a gas shield layer 22 and a trap layer 21 are additionally applied to the air fuel ratio sensor 1 in the first embodiment. The gas shield layer 22 is disposed on the surface of the gas diffusion resistive layer 14, and the gas shield layer 22 and the pump electrode 122 are covered with the trap layer 21. The measurement gas is introduced onto the measurement electrode 111 from side portions 140 of the gas diffusion resistive layer 14 on which the gas shield layer 22 is not disposed. Accordingly, in the present embodiment, temperature dependency of the sensor can be suppressed. The gas shield layer 22 and the trap layer 21 are preferably made of ceramic materials. The other effects and features are the same as those in the first embodiment.

While the present invention has been shown and described with reference to the foregoing preferred embodiments, it will be apparent to those skilled in the art that changes in form and detail may be made therein without departing from the scope of the invention as defined in the appended claims.

What is claimed is:

1. An air fuel ratio sensor for detecting an air fuel ratio of measurement gas using reference gas introduced into a reference gas chamber formed therein, the air fuel ratio sensor comprising:
    a first solid electrolyte body portion having oxygen ion conductivity, the first solid electrolyte body portion having a first surface exposed to the measurement gas and a second surface exposed to the reference gas in the reference gas chamber;
    a second solid electrolyte body portion having oxygen ion conductivity, the second solid electrolyte body portion having a first surface exposed to a gas outside the reference gas chamber and a second surface exposed to the reference gas in the reference gas chamber;
    a measurement cell provided on the first solid electrolyte body portion for detecting the air fuel ratio in the measurement gas, the measurement cell having a measurement electrode disposed on the first surface of the first solid electrolyte body portion and a reference electrode disposed on the second surface of the first solid electrolyte body portion, the measurement electrode and the reference electrode facing one another with the first solid electrolyte body portion interposed therebetween;
    an oxygen pump cell provided on the second solid electrolyte body portion and having a first pump electrode disposed on the first surface of the second solid electrolyte body portion and a second pump electrode disposed on the second surface of the second solid electrolyte body portion, the first and second pump electrodes facing one another with the second solid electrolyte body portion interposed therebetween for introducing oxygen gas from said gas outside the reference gas chamber into the reference gas chamber when a voltage is applied between the first and second pump electrodes; and
    a heating member having first and second lead portions respectively electrically connected to the first and second pump electrodes.

2. The air fuel ratio sensor of claim 1, wherein:
    the first solid electrolyte body portion defines a first solid electrolyte body and said second solid electrolyte body portion defines a second solid electrolyte body, and wherein said first and second solid electrolyte bodies are joined together.

3. The air fuel ratio sensor of claim 2, wherein the first and second solid electrolyte bodies face one another to define the reference gas chamber therebetween.

4. The air fuel ratio sensor of claim 1, further comprising:
    a gas diffusion resistive layer disposed on the measurement electrode of the measurement cell, for restricting the measurement gas from being introduced onto the measurement electrode; and
    a gas shield layer disposed on a surface of the gas diffusion resistive layer except part of a side face of the gas diffusion resistive layer so that the measurement gas is introduced from the side face of the gas diffusion resistive layer onto the measurement electrode.

5. The air fuel ratio sensor of claim 1, further comprising a trap layer disposed on the measurement electrode for trapping contaminations contained in the measurement gas.

6. The air fuel ratio sensor of claim 1, wherein the oxygen pump cell introduces oxygen gas from outside the reference gas chamber into the reference chamber when the voltage applied to the oxygen pump cell is equal to or less than 1V.

7. The air fuel ratio sensor of claim 6, wherein the solid electrolyte body includes zirconia.

8. The air fuel ratio sensor of claim 1, further comprising a heater substrate laminated with the second solid electrolyte body portion,
    wherein the heating member is disposed on the heater substrate.

9. The air fuel ratio sensor of claim 8, wherein;
    the first and second solid electrolyte body portions and the heater substrate together constitute a sensor body; and
    the first and second lead portions of the heating element are respectively connected to the first and second pump electrodes inside the sensor body.

10. The air fuel ratio sensor of claim 1, wherein the heating member is a member distinct from the first and second pump electrodes.

11. An air fuel ratio sensor for detecting an air fuel ratio of measurement gas using reference gas introduced into a reference gas chamber formed therein, the air fuel ratio sensor comprising:
    first and second solid electrolyte bodies having oxygen ion conductivity and facing one another to make the reference gas chamber therebetween, the first solid electrolyte body having first and second surfaces exposed to the measurement gas and exposed to the reference gas chamber respectively, the second solid electrolyte body having first and second surfaces exposed to outside of the reference gas chamber and exposed to the reference gas chamber respectively;

a measurement cell provided on the first solid electrolyte body for detecting the air fuel ratio in the measurement gas;

an oxygen pump cell provided on the second solid electrolyte body for introducing oxygen gas from the outside of the reference gas chamber into the reference gas chamber, the oxygen pump cell having a first pump electrode disposed on the first surface of the second solid electrolyte body and a second pump electrode disposed on the second surface of the second solid electrolyte body, the first and second pump electrodes facing one another with the second solid electrolyte body interposed therebetween; and a heating member disposed on a side opposite to the reference gas chamber with respect to the second solid electrolyte body, the heating member being electrically connected to the oxygen pump cell in parallel.

12. The air fuel ratio sensor of claim 11, wherein the oxygen pump cell introduces the oxygen gas from the measurement gas into the reference gas chamber.

13. The air fuel ratio sensor of claim 11, further comprising an external power supply for applying a voltage to the oxygen pump cell and to the heating member.

14. The air fuel ratio sensor of claim 11, further comprising a heater substrate disposed on the second solid electrolyte body on a side opposite to the reference gas chamber and having a window portion for exposing the first pump electrode to the outside of the reference gas chamber, wherein the heating member is disposed on the heater substrate.

15. The air fuel ratio sensor of claim 14, further comprising a cover plate disposed between the heater substrate and the second solid electrolyte body and having a window portion for exposing the first pump electrode to the outside of the reference gas chamber, wherein the heating member is disposed between the heater substrate and the cover plate.

16. The air fuel ratio sensor of claim 11, wherein;

the heating member has first and second lead portions respectively electrically connected to the first and second pump electrodes; and the oxygen pump cell receives a voltage through the first and second lead portions of the heating member.

17. The air fuel ratio sensor of claim 11, wherein the heating member is a member distinct from the first and second pump electrodes.

18. An air fuel ratio sensor comprising:

a first solid electrolyte body portion having oxygen ion conductivity, said first solid electrolyte body portion having a first surface exposed to a measurement gas and having a second surface;

a second solid electrolyte body portion having oxygen ion conductivity, the second solid electrolyte body portion having a first surface and a second surface;

a reference gas chamber defined in part by said second surface of said first solid electrolyte body portion and in part by said second surface of said second solid electrolyte body portion;

a measurement cell provided on the first solid electrolyte body portion for detecting an air fuel ratio of the measurement gas using reference gas introduced into said reference gas chamber, the measurement cell having a measurement electrode disposed on the first surface of said first solid electrolyte body portion and a reference electrode disposed on the second surface of the first solid electrolyte body portion, the measurement electrode and the reference electrode facing one another with the first solid electrolyte body portion disposed therebetween;

an oxygen pump cell provided on the second solid electrolyte body portion and having a first pump electrode disposed on said first surface of the second solid electrolyte body portion and a second pump electrode disposed on the second surface of the second solid electrolyte body portion, the first and second pump electrodes facing one another with the second solid electrode body portion interposed therebetween for introducing oxygen gas from an outside fluid to which said first surface of said solid electrolyte body portion is exposed to the reference gas chamber when a voltage is applied between the first and second pump electrodes; and a heating member having first and second lead portions respectively electrically connected to said first and second pump electrodes.

19. The air fuel ratio sensor of claim 18, wherein the first solid electrolyte body portion and the second solid electrolyte body portion are laminated in opposed facing relation with said reference gas chamber defined therebetween.

20. The air fuel ratio sensor of claim 19, further comprising a reference gas chamber defining plate interposed between said first and second solid electrolyte body portions.

* * * * *